US008010295B1

(12) United States Patent (10) Patent No.: US 8,010,295 B1
Magness et al. (45) Date of Patent: Aug. 30, 2011

(54) SYSTEM AND METHOD FOR SELECTIVELY CLASSIFYING A POPULATION

(75) Inventors: Charles L. Magness, Seattle, WA (US); Shawn P. Iadonato, Seattle, WA (US)

(73) Assignee: IB Security Holders LLC, Seattle, WA (US)

( * ) Notice: Subject to any disclaimer, the term of this patent is extended or adjusted under 35 U.S.C. 154(b) by 1674 days.

(21) Appl. No.: 09/707,576

(22) Filed: Nov. 6, 2000

(51) Int. Cl.
*G01N 33/48* (2006.01)
*C12Q 1/00* (2006.01)
(52) U.S. Cl. .............................................. 702/19; 435/4
(58) Field of Classification Search ........ 705/7; 600/300; 436/6, 63; 702/19; 703/11
See application file for complete search history.

(56) References Cited

U.S. PATENT DOCUMENTS

| | | | | | |
|---|---|---|---|---|---|
| 4,863,873 | A | * | 9/1989 | Matson | 205/780.5 |
| 5,387,506 | A | * | 2/1995 | Blumenfeld et al. | 435/6 |
| 5,753,441 | A | * | 5/1998 | Skolnick et al. | 435/6 |
| 5,953,727 | A | | 9/1999 | Maslyn et al. | 707/104 |
| 5,966,711 | A | | 10/1999 | Adams | 707/104 |
| 6,023,659 | A | | 2/2000 | Seilhamer et al. | 702/19 |
| 6,059,724 | A | * | 5/2000 | Campell et al. | 600/300 |
| 6,130,042 | A | * | 10/2000 | Diehl et al. | 435/6 |
| 6,558,955 | B1 | * | 5/2003 | Kristal et al. | 436/63 |

FOREIGN PATENT DOCUMENTS

| | | |
|---|---|---|
| WO | WO 93/12255 | 6/1993 |
| WO | WO 00/51053 | 8/2000 |

OTHER PUBLICATIONS

"Susceptibility to Breast Cancer," Clinical Study sponsored by National Cancer Institute (NCI) started on Feb. 8, 2000, [retrieved from Internet].*
"Genetic Testing for Breast Cancer Risk: It's Your Choice," NCI, Aug. 14, 1997, [retrieved from Internet].*
Schwartz et al. "Risk Communication in Clinical Practice: Putting Cancer in Context," Journal of the National Cancer Institute Monographs, 1999, [retrieved from Internet].*
Costantino et al. "Validation Studies for Models Predicting the Risk of Invasive and Total Breast Cancer Incidence," Journal of National Cancer Institute, Sep. 15, 1999.*
Archived version of the National Cancer Institute's Breast Cancer Risk Assessment Tool, Jun. 20, 2000 [archived on www.archive.org].*
Hudson, Thomas "The human genome project: Tools for the identification of disease genes," Clinical and Investigative Medicine, Dec. 1998, [retrieved from Proquest].*
Khoury, Muin. "From genes to public health: The applications of genetic technology in disease prevention," American Journal of Public Health, Dec. 1996, [retrieved from Proquest].*
Hunter, David. "The future of molecular epidemiology," International Journal of Epidemiology, Oct. 1999, [retrieved from Proquest].*
Wade, Nicholas. "DNA chips join anti-cancer fight Devices monitor genetic mutations," Denver Post, Apr. 8, 1997, [retrieved from Proquest].*
Emilien et al. "Impact of genomics on drug discovery and clinical medicine," Jul. 2000, [retrieved from Internet].*
Sharp et al. "Involving study populations in the review of genetic research," The Journal of Law, Medicine & Ethics, Spring 2000, [retrieved from Proquest].*
Chow et al. "Effect of Tamoxifen on Mammographic Density," Sep. 2000, [retrieved from Internet].*
Slattery et al. "A comprehensive evaluation of family history and breast cancer risk." Oct. 6, 1993, [retrieved from Internet].*
Rosenthal et al. "Screening for Genetic Risk of Breast Cancer," Jan. 1, 1999, [retrieved from Internet].*
Spiegelman et al. "Validation of the Gail et al. model for predicting individual breast cancer risk." Apr. 20, 1994, [retrieved from Internet].*
Holtzman et al. "Final Report of the Task Force on Genetic Testing," Sep. 1997, [retrieved from Internet].*
"New Genetic Mutation Linked to Breast Cancer," Doctor's Guide, Aug. 31, 1998, [retrieved from Internet].*
Colditz et al. "Family history, age, and risk of breast cancer." Jul. 21, 1993 [retrieved from Internet].*
Ntais et al., "Meta-Analusis of the association of the Cathepsin D Ala224Val Gene Polymorphism with the Risk of Alzheimer's Disease: A HuGE Gene-Disease Association Review," American Journal of Epidemiology, vol. 159 (2004), pp. 527-536.*
Fowke et al., "Resistance to HIV-1 Infection Among Persistently Seronegative Prostitutes bin Nairobi, Kenya." Lancet, England 348(9038):1347-1351, Nov. 16, 1996.
Olson, "Molecular Evolution '99 When Less is More: Gene Loss as an Engine of Evolutionary Change," Am. J. Hum. Genet, 64:18-23, 1999.
Fowke, K. R. et al., Resistance to HIV-1 Infection Among Persistently Seronegative Prostitutes in Nairobl,, Kenya, The Lancet 348:1347-1351, 1996.
Lin, P. et al., NAD(P)H: Quinone Oxidoreductase Polymorphism and Lung Cancer in Taiwan, J. Toxicoloty and Environmental Health, Part A, 58187-197, 1999.
Lin, P. et al., NAD(P)H: Quinone Oxidoreductase Polymorphism and Lung Cancer in Taiwan, Journal of Toxicology and Environmental health, Part A, 58:187-197, 1999.

(Continued)

*Primary Examiner* — Marjorie Moran
*Assistant Examiner* — Anna Skibinsky
(74) *Attorney, Agent, or Firm* — K&L Gates LLP; C. Rachal Winger

(57) ABSTRACT

A technique is disclosed for classifying a population of subjects into various sub-populations for a selected biological condition. Patients are categorized in accordance with numeric scores for a affected status for the selected biological condition and a risk status for the selected biological condition. The numeric scores for an overall population are determined in advance for the selected biological condition. Medical test results, including genetic tests, and risk factors are numerically scored and may further be weighted in accordance with their relevance in determining affected status and risk. Medical test results and medical histories for individual subjects within the population may then automatically be scored in accordance with the predefined characteristics. The numerical scores for affected status and risk status may be stored in a data structure, such as a database. The numeric scores are extracted from the data structure and used to classify individuals in the population into one of a group of selected sub-populations comprising at-risk affected (ARA) and at-risk unaffected (ARU). Additional sub-populations, such as unknown risk, unaffected (URU) may also be used.

48 Claims, 8 Drawing Sheets

OTHER PUBLICATIONS

Drews, J., Genomic Sciences and the Medicine of Tomorrow, *Nature Biotechnology 14*:1516-1517, 1996.

Bumol, T. F. and Watanabe, A. M., Genetic Information, Genomic Technologies, and the Future of Drug Discovery, *JAMA 285*(5):551-555, 2001.

Dean et al., *Genetic Restriction of HIV-1 Infection and Progression to AIDS by a Deletion Allele of the CKR5 Structural Gene*, Science (273):1856-1862, 1996.

* cited by examiner

SYSTEM AND METHOD FOR SELECTIVELY CLASSIFYING A POPULATION

TECHNICAL FIELD

The present invention is directed generally to biological analysis and, more particularly, to a system and method for classifying a population of subjects based on biologic information.

BACKGROUND OF THE INVENTION

The current state-of-the-art in genomics and genetics involves the use of these technologies to understand the genetic basis of disease. Although these types of studies have proven scientifically interesting and have significantly furthered our understanding of the genetic and biochemical basis of inherited illness, they have had little effect on the economic commercial development of mass-market drugs. As a result, the promise of genomics as an enabling technology in the development of new and improved clinical compounds has remained unrealized.

This difficulty derives from the fundamental fact that disease genes and drug target genes belong to entirely different classes of genomic targets with little intersection between the two groups. For example, it is known that a loss-of-function (LOF) mutation in a gene, identified as BRCA1, increases the risk for breast cancer. While this knowledge is of great importance to cancer biology, it does little to accelerate the development of new drugs to treat breast cancer. This is because most drugs are antagonists. That is, the drugs cause a loss-of, or interference, with protein function, so that any drug that inhibits the function of the BRCA1 gene or its associated protein is more likely to increase the risk for breast cancer than reduce it. Gene therapy or protein replacement therapy may offer a path forward, but the prevailing paradigm is that a disease gene is a handle onto a biochemical pathway that will ultimately lead to a new drug target. This leap of faith, despite significant historical investment, has resulted in the development of few, if any, new pharmaceutical compounds.

For this very reason, recent efforts to use genomics as a tool for drug development have had disappointing results, primarily due to a focus on disease gene identification as an essential first step in the drug development process. A dramatic, but by no means unique example of this is the cloning and characterization of the mutation in the gene responsible for cystic fibrosis. Cloning of the cystic fibrosis transmembrane conductance regulator (CFTR) gene was a watershed in human genetics, as it was the first time that a gene for a genetic illness was cloned entirely using positional cloning (genomic-genetic) technologies. Collins, F. S., Drumm, M. L., Cole, J. L., Lockwood, W. K., Vande Woude, G. F., and Iannuzzi, M. C., *Science* 235(4792):1046-9 (1987).

When the discovery of the gene was reported in 1989, a treatment for the disease was believed to lie just around the corner. Unfortunately, many researchers underestimated the complexity of deciphering the CFTR biochemical pathway, and of developing new drugs or gene therapies to treat the most common inherited deficiency in the CFTR gene. In fact, in more than a decade since the discovery of CFTR, only two major new drugs to treat cystic fibrosis have been developed. Neither of these drugs, Tobramycin and Pulmozyme, were developed by relying on specific knowledge of the cystic fibrosis-causing genetic defect. Although genomics has been a powerful tool for understanding the cause of many simple, inherited human illnesses, it has been less effective at identifying and validating drug targets for the pharmaceutical industry.

The focus on the disease process and the identification of genes associated with disease have led to unsatisfactory results. Present efforts have focused on segments of the population afflicted by a particular disease. Therefore, it can be appreciated that there is a significant need for techniques that rely on the analysis of phenotypes other than the disease phenotype, thereby enabling the identification of validated drug targets and the development of new diagnostics and vaccines. The present invention provides this and other advantages as will be apparent from the following detailed description and accompanying figures.

SUMMARY OF THE INVENTION

The present invention is directed to a method and system for classifying populations of subjects. In an exemplary embodiment, the method comprises analyzing the medical histories of a population and analyzing medical or biochemical test results for members of the population. Based upon the medical histories and medical or biochemical test results, each population member is classified into one of a group of sub-populations for a selected biological condition. The subjects in the population are classified as "at-risk and affected" (ARA) by the selected biological condition and "at-risk and unaffected" (ARU) by the selected biological condition. For statistical evaluation purposes, another phenotypic group, unknown risk and unaffected (URU) for the selected biological condition may also be designated.

In one embodiment, the analysis of medical histories comprises assigning numerical scores to selected medical observations, risks, and/or behaviors that are associated with the selected biological condition. In addition, analysis of medical test results may also comprise assigning numerical scores to selected medical test results associated with the selected biological condition. The medical test results may include genetic and/or biochemical testing. The classification of the population into sub-populations may comprise evaluating the numerical scores for medical histories and/or medical test results. In one embodiment, the numerical scores for medical histories and medical test results may be combined and the classification of the population based on combined numerical scores.

In another embodiment, the method may further comprise generating statistical data related to numerical scores for medical histories and/or medical test results wherein the classification of the population comprises analyzing the statistical data. The statistical data may further comprise generating a frequency distribution plot related to numerical scores for the medical histories and/or medical test results. In this embodiment, the population is classified into sub-populations based on the frequency distribution plot.

In yet another aspect of the invention, the medical histories and medical test results of the sub-population classified as ARU are compared with the medical histories and medical test results of the sub-population classified as URU. The method may further comprise determining genetic differences between genetic test results of the sub-population classified as ARU with the genetic test results of the sub-population classified as URU.

Alternatively, medical histories and/or medical test results of the sub-population classified as ARU may be compared with the medical histories and/or medical test results of the sub-population classified as ARA. The medical test results may comprise genetic test results. In this embodiment, the genetic test results of the sub-population classified as ARU may be compared with the genetic test results of the sub-population classified as ARA.

DETAILED DESCRIPTION OF THE INVENTION

Figure 1:
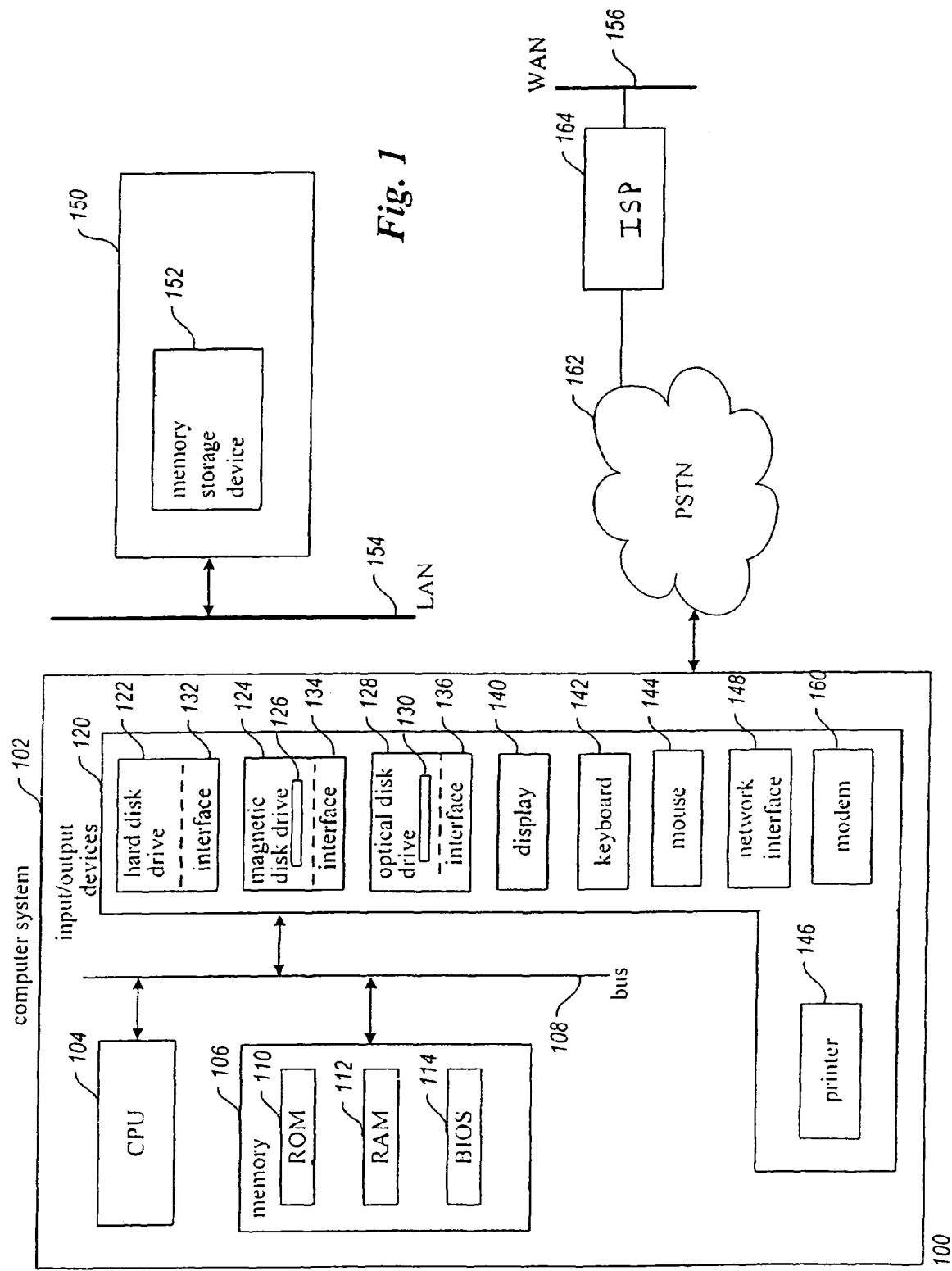
FIG. 1 is a block diagram of a computer system capable of implementation of the present invention.

The present invention describes an alternative to the historical use of genomics in the drug development process as a tool to understand disease and predict risk thereof. Rather than using genomics to understand why some people become sick, the present invention describes a process to determine the genetic influences that allow people to remain healthy, even under conditions where they are expected to be sick. Such disease-associated conditions are hereafter termed risk factors and may contain without limitation any combination of known or hypothesized a) host factors (for example, genetic predisposition and anthropometry); b) environmental factors (for example, socioeconomic status and lifestyle); or c) causative agent exposures (for example, viral exposure). By using genomics to identify mutations that lead to a healthy rather than a diseased phenotype, the present invention provides a more efficient and directed process for identifying highly validated drug targets.

A technique, known as Replicated Natural Resistance To Disease™, or RNR, is a new genomics-based data processing strategy for the ready identification of highly validated candidate drug targets. This invention describes a process by which specific populations of human subjects are ascertained and analyzed in order to discover naturally occurring genetic variations (or mutations) that confer resistance to disease. The term "mutation" refers to changes in genetic material that may be present in single individuals or within a population of individuals. This term may also be referred to as "polymorphisms" to indicate a range of genetic variations among individuals in a population. As will be described below, the present invention classifies a study population into groups and analyzes genetic differences between groups. These genetic differences may alternatively be referred to as mutations, polymorphisms or variants. The identification of a sub-population segment that has a natural resistance to a particular disease or biological condition further enables the identification of genes and proteins that are attractive targets for pharmaceutical intervention, diagnostic evaluation, or prevention (e.g. prophylactic vaccination). By emphasizing an analysis of the genetic basis of disease resistance or "health," the present invention also enables a faster and more cost-efficient approach to identifying and validating protein targets for pharmaceutical development (both therapeutic and prophylactic). Furthermore, therapeutic intervention would be presumed to show acceptable patient tolerance, as the desired outcome is to mimic the natural resistance phenotype of healthy individuals.

In one aspect, the invention describes the parsing of a population into selected phenotypic groups: (1) those affected individuals who have a clinical phenotype characteristic of a particular disease, the "at-risk, affected" or ARA phenotypic group, and (2) those apparently resistant individuals who have been exposed to significant risk but have failed to contract the disease, the "at risk, unaffected" or ARU phenotypic group.

As will be discussed in greater detail below, large segments of a population may not fall into either of these two phenotypic groups. For purposes of statistical evaluation, it may be desirable to create a third phenotypic group to include those unaffected individuals of unknown risk or exposure status who have a normal phenotype, the "unknown risk, unaffected" or URU phenotypic group. The URU group may serve as a control group for purposes of statistical evaluation of genetic mutations among the individuals in the other phenotypic groups.

The present invention is directed to a technique for identifying and characterizing relevant populations and classifying individuals into one of the three phenotypic groups described above. The proper classification of individuals in a population can lead to a better understanding of the genetic mechanisms that allow an individual to remain healthy despite significant risk exposure, and can thus lead to the development of drugs that mimic the effects of genetic variations and genes responsible for the ARU phenotype. For example, cardiovascular disease research has traditionally focused on the study of individuals with high levels of serum cholesterol. Treatments that reduce the level of cholesterol in the blood are known to reduce the risk of heart attack and other coronary artery diseases and to increase longevity in patients treated with these drugs.

Several recent studies have been reported that were designed to evaluate the distribution of cholesterol levels in the human population and to relate these levels to environmental and lifestyle factors. Interestingly, in each of these studies, a small group of relatively rare individuals (~1-2%) was found to have consistently very low levels of circulating serum cholesterol. Snyder, S. M., Terdiman, J. F., Caan, B., Feingold, K. R., Hubl, S. T., Smith, R. S., and Young, S. G., *American Journal of Medicine* 95(5):480-8 (1993); Sonnenberg, L. M., Quatromoni, P. A., Gagnon, D. R., Cupples, L. A., Franz, M. M., Ordovas, J. M., Wilson, P. W., Schaefer, E. J., and Millen, B. E., *Journal of Clinical Epidemiology* 49(6): 665-72 (1996); Glueck, C. J., Kelley, W., Gupta, A., Fontaine, R. N., Wang, P, and Gartside, P. S., *Metabolism* 46(6):625-33 (1997); Iribarren, C., Jacobs, D. R., Slattery, M. L., Liu, K., Sidney, S., Hebert, B. J., and Roseman, J. M., *Preventive Medicine* 26:495-507 (1997); Welty, F. K., Lahoz, C., Tucker, K. L., Ordovas, J. M., Wilson, P. W. F., and E. J. Schaefer, *Arteriosclerosis, Thrombosis, and Vascular Biology* 18:1745-51 (1998). An analysis of the lifestyle patterns of these individuals relative to the patterns found in the rest of the population showed little correlation between stably-low serum cholesterol and exercise, diet, or other obvious cardiovascular risk factors. While it is possible that unknown environmental or lifestyle-related risk factors are the cause of this stably-low serum cholesterol phenotype, the natural resistance concept assumes that the likeliest cause is the presence of a favorable genetic makeup in these rare, super-healthy individuals.

Given that humans have evolved for many hundreds of thousands of years in an environment where food and energy resources were limiting, the development of a very energy-efficient metabolism, where serum cholesterol levels were maximized, was likely to have been favored. Mutations in the genes responsible for this energy-efficient metabolism would lead to low serum cholesterol levels. Individuals with very low levels of serum cholesterol would not have survived the long periods of fasting suffered by our ancestors throughout much of early human evolution. However, in our modern society where food is in abundance, the loss of an energy-efficient metabolism by mutation confers a beneficial or super-healthy phenotype. Individuals who carry such mutations now become resistant to cardiovascular disease and have an elongated life-span. The goal of the present invention is to identify the desired sub-population of at-risk, but unaffected individuals so as to permit an analysis of those individuals and thereby determine a genetic basis for their unexpected health.

The present invention describes the use of medical histories and medical tests, including genetic tests, to identify a sub-population having an at risk unaffected ARU phenotype. By comparing individuals in the ARU phenotypic group with individuals classified into other groups (e.g., ARA and URU), genomic and genetic technologies can be used to identify the protective polymorphisms and/or mutations that are responsible for the ARU phenotype. The biochemical effect of these mutations can be mimicked or replicated therapeutically, thereby conferring the same beneficial phenotype in a normal, clinical population.

For example, if a protective mutation impairs or prevents proper function in a specific protein in the ARU population, an antagonistic small molecule or peptide drug may be developed against the same protein, thereby preventing its function and conferring a clinical benefit in an otherwise susceptible population. Similarly, protective mutations that improve or provide novel protein function may be replicated in a susceptible population using gene or protein replacement therapy.

Furthermore, the specific genotype defining the protective mutation provides the comparative basis for the development of diagnostic tests. In one embodiment of a diagnostic test, a laboratory assay compares the genotype of one subject against the known protective mutation genotype; a positive match may indicate that the test subject is protected against (i.e., immune or less susceptible to) the disease in question.

Clinical Population Considerations

The RNR process involves identifying a study population that contains representatives of each of the three phenotypically-defined sub-populations (ARA, ARU, and URU) for the biological condition of interest. It should be noted that the term "biological condition" refers to a biological state, disease, physiological condition or the like. These terms may be used interchangeably throughout the application. The present invention is not limited to any specific biological condition. In one embodiment of this approach, the study population may be a geographically defined population that is managed by a clinical physician(s). In another embodiment, the study population may be a combination of several geographically- and/or behaviorally-distinct populations. In yet another embodiment, some or all of the study population may be recruited de novo to provide additional representation for any or all of the three phenotypically-defined sub-populations. In populations with significant disease penetrance, the phenotype defined as ARU may account for only a small minority of all population members.

The ideal study population will have a well-defined group of individuals that, despite having well documented risk factors, remain healthy or uninfected. Furthermore, the study population is chosen so that the absolute number of potential ARU members may provide statistically significant relative allele frequencies in genetic studies as defined below. A number of different types of statistical techniques may be applied to the data to determine statistical relevance. For example, reliable detection (95% confidence interval) of alleles represented at 1% frequency or greater in the ARU sub-population can be used to determine an adequate population size. Alternatively, one could define the necessary population size as one that would allow the statistically significant detection of a 10% or greater difference in allele frequency when the same allele is compared between any two of the three relevant sub-populations (AIM, ARU, or URU). However, those skilled in the art will recognize that other statistical measures may be employed to assure adequate population size. The present invention is not limited by the selected statistical technique.

The present invention is directed to techniques for deriving sub-populations of individuals from a larger population based upon a health-related phenotype. Subsequent to segregation of the population into the three phenotypic sub-groups (i.e., ARA, ARU, URU), information is collected regarding the presence and frequency of variants in a panel of candidate genes as ascertained from members of the three newly-defined sub-populations. The emphasis is on discovering genetic variants that are present in, and confer resistance to disease upon, members of the ARU sub-population. By identifying the genetic variants that confer resistance to disease in the ARU sub-population, the invention provides a method for identifying and validating novel drug targets and for enabling the development of unique diagnostic tests.

As can be appreciated, the characteristics of an ARU phenotype will vary from one biological condition to another. For example, individuals having low serum cholesterol, as described above, can be identified on the basis of conventional biochemical analysis. Other medical and genetic tests may also be performed. In contrast, individuals that appear to possess an ARU phenotype for human immunodeficiency virus (HIV) may be classified in accordance with other medical tests, such as antibody seroconversion assays and viral load measurements. In addition, various aspects of medical histories, such as lifestyle, environmental or infectious disease exposure, and host genetic factors play an important role in classifying individuals into a particular sub-population. The relative risk ascribed to various factors will also vary from one disease or condition to another. For example, diet may be a strong risk factor in defining phenotype relative to cholesterol levels and heart disease, but of little interest when segregating populations relative to a sexually transmitted or blood-borne disease such as HIV. Additional details regarding clinical evaluation are provided below.

A clinical protocol is developed for each population that includes a comprehensive epidemiological, biochemical, and where appropriate genetic study specifically tailored to the disease of interest. The protocol clearly resolves the phenotype through examination of risk factors and other clinical and epidemiological measurements. Greater statistical power is obtained thorough a more rigorous examination of each risk factor and by narrowly defining the ARU phenotype.

Mutation Identification and Analysis

Following the classification of population members according to phenotype, genomic DNA is recovered from each patient. DNA samples are analyzed to determine composite genotypes across a set of candidate genes for each individual. The invention is not limited by the scope or number of the candidate genes analyzed. Each genotype is resolved to the individual DNA base-pair level. In one implementation of this analysis, sets of polymerase chain reaction (PCR) primers that allow amplification of the functional (i.e., coding or regulatory) regions of each candidate gene are developed. PCR amplification is used to recover candidate gene sequences from each patient. Purified PCR products are subjected to DNA sequence analysis, and mutations are detected in diploid-derived sequencing traces. Other appropriate methods for specific gene sequence recovery may also be used to determine patient genotypes to single base-pair resolution.

Thereafter, loss-of-function or other functionally important mutations that are identifying markers for drug target genes are discovered through a combination of informatics-based functional and statistical genetics analysis. Each patient's candidate gene sample sequence is compared to a reference sequence to identify all sequence mutations or variants. The invention is not limited to the identification of mutations present in either the homozygous or heterozygous state.

The value of individual mutation analysis has been described above. However, mutations can also be analyzed on the basis of functionality. Each unique observed mutation may be classified into a functional variant group, based upon the computed effect on eventual gene product activity. The functional variant groups (or "functional bins") are defined on the basis of a variety of distinguishing effects including but not limited to: null expression; prematurely truncated gene product; malformed primary transcript due to mis-splicing or poly-A recognition site modification; or site-specific mutations leading to modified gene product activity. Variants that share similar functional consequences are grouped together in a functioned "bin." Such grouping allows for an increased likelihood of associating a functional bin with the ARU phenotype. An example of this would be the grouping together into a single functional bin of several DNA mutations coding for synonymous codon substitutions within a translated protein. Another example of a functional bin would be the grouping together of distinct nonsense mutations at several closely spaced sites that lead to premature truncation of the primary RNA transcript.

Variant Association Test

In one embodiment, statistical genetics is used to evaluate the relationship between each observed candidate gene variant and the ARU phenotypic group. The frequency, $f_A$, of each newly identified candidate gene variant is determined both in the ARU group (denoted $f_{A,ARU}$) and a control group defined below (denoted $f_{A,CTL}$). In each case, the frequency is defined as the number of patient alleles (properly accounting for two parental alleles in each patient) observed to possess the allele of interest in the group of interest divided by the total number of patient alleles in that group. The relative ratio of allele frequencies ($r_A$) between the ARU and control groups is also determined ($r_A = f_{A,ARU}/f_{A,CTL}$). The term "control group" refers to any population whose genetic characteristics will be compared to those of the ARU group. The control group may be either one of the previously defined phenotypic groups (e.g., the ARA group), a combination of phenotypic groups, or some other population or control group.

The probability that the result $r_A$ could occur from random sampling bias is also calculated to estimate the statistical significance of the ratio $r_A$. In the simplest monogenic or single gene model, a single gene effect contributes solely to the disease resistance phenotype. In these cases, a statistically significant deviation of $r_A > 1.0$ is an indication of relatedness between the candidate gene variant under study and the ARU phenotype. This implies that either the gene variant under consideration confers a protective resistance to the biological condition, or is in linkage disequilibrium with another variant that provides such resistance.

Functional Bin Association Test

In another embodiment, a similar analysis is conducted to test association of a given functional bin with the ARU group. In this case, the functional bin frequency, $f_{FA}$, is calculated in the ARU ($f_{FA,ARU}$) and control ($f_{FA,CTL}$) groups. Also, the ratio of functional bin frequencies, $r_{FA}$, between the ARU group and the control group is determined (($r_{FA} = f_{FA,ARU}/f_{FA,CTL}$). The statistical significance of the result is also determined, and a statistically significant $r_{FA} > 1.0$ is an indication of association between the functional bin and the ARU phenotype. In this instance, however, if the functional bin is observed as more than one distinct mutation, the likelihood is increased that the functional bin is directly associated with the ARU phenotype and not confounded by linkage disequilibrium issues. One skilled in the art can appreciate that this effect, combined with the statistical enhancement gained by functional binning, provides considerable advantage over variant association alone. Taken together, the variant association and the functional bin association tests may provide considerable evidence as to which variants and candidate genes are associated with the ARU phenotype.

As discussed in the foregoing, either individual candidate gene mutations or functional bins or both may be tested for association with the ARU phenotype of interest. The invention is not limited to whether either or both of the aforementioned association tests are performed. The approach of grouping mutations into functional bins increases the likelihood that statistically significant associations may be observed relative to the ARU phenotype.

Further, the invention is not limited by the number of variants, functional bins, or genes that are simultaneously tested for association with the ARU phenotype. Together, these statistical analyses directly indicate one or more putative drug target genes that when functionally modified confer disease resistance.

As those skilled in the art can appreciate, this type of genotypic evaluation is significant within the present invention due to the classification of subjects into the phenotypic categories discussed above. That is, the discovery of genetic drug targets becomes a valuable tool when the ARU phenotype is compared against other sub-populations.

In each of the frequency analyses indicated above, the frequency of a given allele or functional allele is measured in the ARU group relative to a control group. As discussed above, the control group may consist of patients from either the ARA or URU populations, a combination of both groups, or another subject group. The algorithm used to enroll ARA or URU patients into the control population will vary from disease to disease. In one embodiment of this approach, the algorithm may also be impacted by local population factors where multiple geographically or ethnically dispersed populations have been combined together for this study. In general, ARA patients are well suited for controlling the analysis relative to ARU patients, since subjects in the ARA population are presumed not to carry the protective mutation. On the other hand, specificity as compared to the URU group is less certain since at least some subjects in the URU population may carry the protective mutation, but may not have been placed in the ARA group due to an absence of risk factors associated with the condition of interest. However, identification of a protective mutation through comparison of the ARU and ARA groups alone may not be generalizable due to biasing factors, such as ethnicity. As a result, it is essential to ensure that the genetic make-up of the ARA and ARU sub-populations are similar in all respects, except in relationship to the genetic basis of the natural resistance phenotype. In order to confirm this general genetic similarity, allele frequencies are compared among these two groups and the URU subpopulation. Allele frequencies, when compared among all three populations, should not differ significantly for genes that are not causative of, or in linkage disequilibrium with, the natural resistance phenotype.

Based upon a comparison of the ARU sub-population with respect to sub-populations in other classifications, it is possible to determine the gene or genes responsible for the natural resistance phenotype and to develop peptide, small molecule, or antibody-based pharmaceuticals that mimic the effects of these protective polymorphisms. Furthermore, the protective polymorphism may be directly examined by clinical diagnostic assays to assess prospectively whether a given patient may be susceptible to the disease in question.

FIG. 1 and the following discussion are intended to provide a brief, general description of a suitable computing environment in which the invention may be implemented. Although not required, the invention will be described in the general context of computer-executable instructions, such as program modules, being executed by a personal computer (PC). Generally, program modules include hardware, as well as routines, programs, objects, components, data structures, etc. that perform particular tasks or implement particular abstract data types. The invention may be implemented in a distributed computing environment where tasks are performed by remote processing devices that are linked through a communications network. In a distributed computing environment, program modules may be located in both local and remote memory storage devices.

With reference to FIG. 1, an exemplary system 100 for implementing the invention includes a general purpose computing device in the form of a conventional PC 102, including a central processing unit (CPU) 104, a system memory 106, and a system bus 108 that couples various system components, including the system memory 106, to the CPU 104. The system bus 108 may be any of several types of bus structures including a memory bus or memory controller, a peripheral bus, and a local bus using any of a variety of bus architectures. The system bus 108 may also include a power bus. For the sake of convenience, the various busses are illustrated in FIG. 1 as the bus system 108.

The system memory 106 includes read-only memory (ROM) 110 and random access memory (RAM) 112. A basic input/output system 114 (BIOS), containing the basic routines that helps to transfer information between elements within the personal computer 102, such as during start-up, may be stored in ROM 110.

The personal computer 102 further includes input/output devices 120, such as a hard disk drive 122 for reading from and writing to a hard disk, not shown, a magnetic disk drive 124 for reading from or writing to a removable magnetic disk 126, and an optical disk drive 128 for reading from or writing to a removable optical disk 130, such as a CD ROM or other optical media. The hard disk drive 122, magnetic disk drive 124, and optical disk drive 126 are connected to the system bus 108 by a hard disk drive interface 132, a magnetic disk drive interface 134, and an optical drive interface 136, respectively. The disk drives and their associated computer-readable media provide nonvolatile storage of computer readable instructions, data structures, program modules and other data for the personal computer 102. Although the exemplary environment described herein employs a hard disk, a removable magnetic disk 126 and a removable optical disk 130, it should be appreciated by those skilled in the art that other types of computer readable media which can store data that is accessible by a computer, such as magnetic cassettes, flash memory cards, digital video disks, Bernoulli cartridges, random access memories (RAMs), read-only memories (ROM), and the like, may also be used in the exemplary operating environment.

The personal computer 102 may also include other I/O devices 120, such as a display 140, keyboard 142, mouse 144 and printer 146. The operation of these I/O devices 120 are well-known, and need not be described in greater detail, except as it relates to the operation of the present invention. Additional I/O devices, such as a joystick, sound board, speakers and the like may be included in the personal computer 102. For the sake of brevity, these components are not illustrated in FIG. 1.

The personal computer 102 may also include a network interface 148 to permit operation in a networked environment using logical connections to one or more remote computers, such as a remote computer 150. The remote computer 150 may be another personal computer, a server, a router, a network PC, a peer device or other common network node, and typically includes many or all of the elements described above relative to the personal computer 102, although only a memory storage device 152 has been illustrated in FIG. 1. The logical connections depicted in FIG. 1 include a local area network (LAN) 154 and a wide area network (WAN) 156. Such networking environments are commonplace in offices, enterprise-wide computer networks, intranets and the Internet.

When used in a LAN networking environment, the personal computer 102 may be connected to the LAN 154 through the network interface 148. When used in a WAN networking environment, the personal computer 102 typically includes a modem 160 or other means for establishing communications over the WAN 156, such as the Internet. The modem 160, which may be internal or external, permits communication with the WAN 156 via a telephone network 162, such as a public switched telephone network (PSTN). FIG. 1 illustrates the modem 156 as coupled to an Internet service provider (ISP) 164 via the PSTN 162. The ISP 164 serves as a gateway to the WAN 156, such as the Internet. It will be appreciated that the network connections shown are exemplary and other means of establishing a communications link between the computers may be used. For example, a network PC is often connected to the WAN 156 through the LAN 154.

Figure 2:
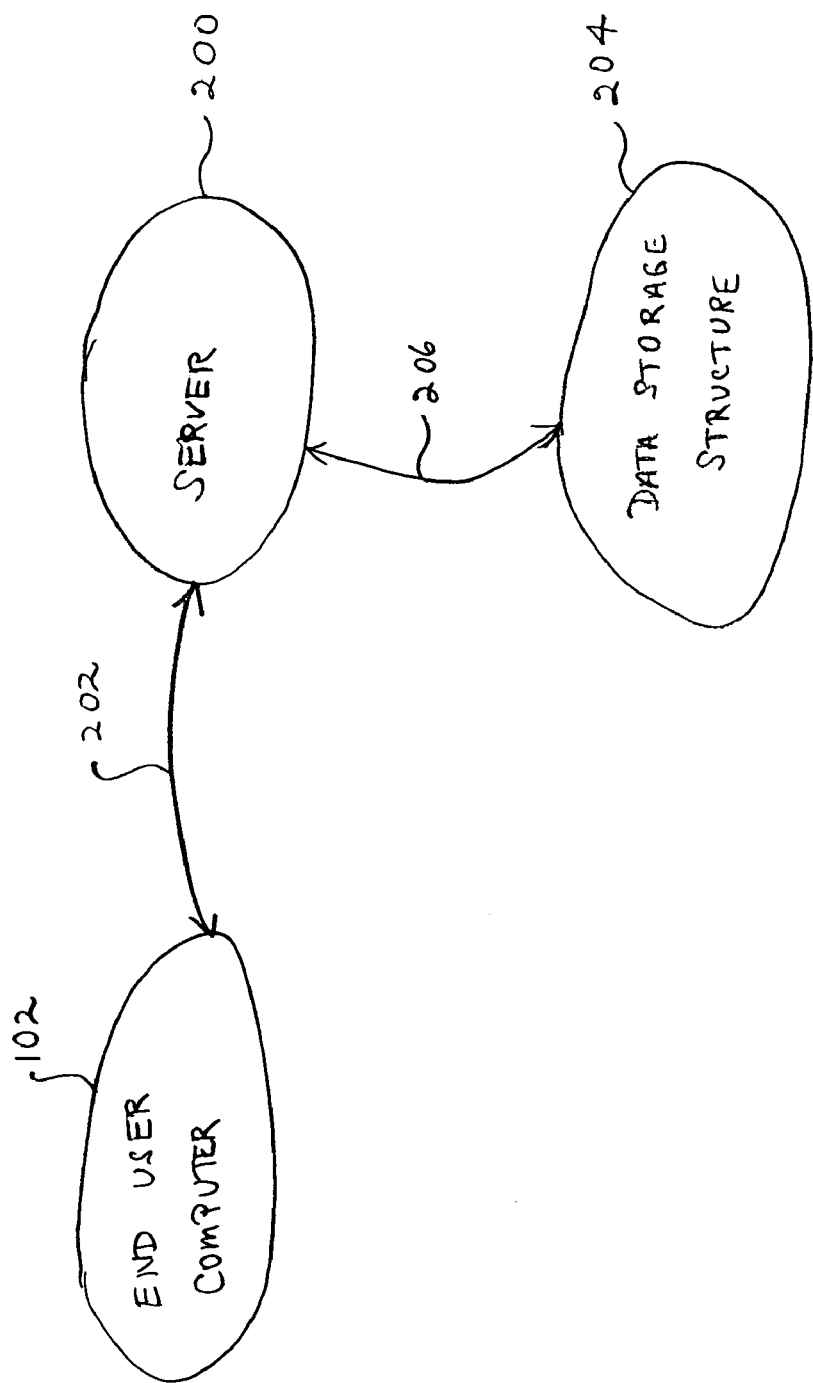
FIG. 2 is a block diagram illustrating the flow of communications between system components in a computer network implementation of the system of the present invention.

FIG. 2 illustrates the flow of communication in a sample implementation of the present invention. An end user, using a computer, such as the computer system 102, communicates with a server 200 via a communication link 202. The communication link 202 may be implemented via the LAN 154 (see FIG. 1), the WAN 156, or the like. The present invention is not limited by the specific form of the communication link 202. A data storage structure 204 is associated with the server 200 and communicates with the server via a communication link 206. The data storage structure 204 may be implemented using any convenient known form of data structure, such as a database, data table, or the like. The present invention is not limited by the specific form of the data storage structure 204. The data storage structure 204 may be an integral part of the server 200, such as a memory storage device 152 (see FIG. 1). Alternatively, the data storage structure 204 may be located remotely from the server 200 and accessible via a communication link 206, such as the LAN 154 or the WAN 156. The present invention is not limited by the specific form of the communication link 206. As will be described in greater detail below, the data storage structure 204 contains: a). data and analytical results for medical risk and affected status for a selected biological condition; b). data and analytical results relating to the candidate genes suspected to be relevant to the selected biological condition; c). data and analytical results thereof collected from genetic and genomic analysis of samples from patients enrolled in the study populations; and d). computer executable code allowing for the processing and analysis of the above data.

Clinical Sample Collection

Populations including high-risk and other individuals are identified and evaluated for their potential usefulness to the study. In one embodiment of this approach, existing populations are identified through associated clinicians, by accessing and evaluating existing clinical data, and by developing a risk model for the population. In another embodiment, individuals are enrolled de novo into the populations based upon pre-defined criteria. Attractive populations will demonstrate an easily identifiable (ARU) sub-population.

(1) Identify Populations with High-Risk Individuals

Populations or clinical study groups of between several hundred to several thousand individuals in size are identified. In one embodiment, populations are selected where the median phenotypic risk profile falls within the normal to high-risk range. In another embodiment, a more balanced distribution of risk in the overall population may be acceptable or desired. Phenotypic risk is determined through one or more of the following methods:

(a) direct epidemiological study of the population of interest.

(b) collaboration with researchers, clinics, or other institutions that possess direct knowledge of the epidemiological risk-profile of the population of interest.

(c) comprehensive analysis of the literature as it pertains to specific clinical study groups or populations.

Ideal populations demonstrate epidemiological evidence of a population subgroup that is at significant risk for disease, but either unaffected or super-healthy in relation to the biological condition of interest. For instance, in the case of disease associated with high serum cholesterol levels (e.g., heart disease, stroke, coronary artery disease), populations are identified where the median serum cholesterol level for the population is either normal or elevated relative to normal. Ideal populations further demonstrate the presence of a phenotypically stable subgroup of super-healthy (ARU) individuals; that is individuals with very low serum cholesterol over long-duration monitoring. In the case of hepatitis C (HCV) infection, populations that include individuals at high-risk for contracting HCV are identified (e.g., injecting drug users and hemophiliacs). These populations ideally contain a sub-group of high-risk individuals who have failed to become infected with HCV.

(2) Additional Considerations for Population Selection or Development

Well-studied normal to high-risk populations are favored. Although not necessary for implementation of the invention, highly desirable populations have the following characteristics in addition to the ones discussed above:

(a) Populations have been studied for the phenotype of interest for a period of one year or more. The advantage of a well-studied population is that the phenotypic characteristics associated with the selected biological condition are well defined.

(b) Population members have long and well-documented relationships with clinical researchers and the medical community. The advantage of a long-established relationship is that significant amounts of medical test data and patient history data are available to assist in the classification of population members into one of the previously discussed phenotypic groups.

(c) Comprehensive medical records for members of the population are easily accessible. Easy access to medical records provides a ready source of data that can be used to distinguish among individual members of a population. As will be discussed in greater detail below, numerical scores may be assigned to various medical conditions and test results based on scientific data collected for a particular disease or biological condition of interest. These test scores may then be applied to medical histories and medical test results to objectively classify individuals for their risk and affected status for the selected biological condition.

(d) Scientists, clinicians, and healthcare providers with primary access to and experience with the populations of interest are available. Such experience enables the easy collection of medical history data as well as medical test data. Those skilled in the art will appreciate that the advantages discussed above simplify the process of data collection for analysis. However, the characteristics described above are merely desirable, but not necessary for satisfactory implementation of the present invention.

Although not pertinent to proper understanding of the present invention, those with knowledge of clinical medicine will appreciate that informed consent of the patient population and other legal documents may also be required in order to obtain and evaluate medical test results and to obtain the appropriate medical histories. The availability of or ease in acquiring such consent may be a significant consideration in population selection.

(3) Access and Obtain Population Clinical and Epidemiological Data

Population epidemiological records and individual patient data are culled from the following sources:

(a) patient medical records;
(b) patient family histories;
(c) patient interviews; and
(d) epidemiological data previously collected from clinical scientists.

These data will be entered into the predefined data structure 204 (see FIG. 2) in a manner described in greater detail below.

(4) Recover Blood and Biopsy Samples (a) Blood or tissue samples are recovered from individual patients and used as the starting material for DNA recovery. Recovered DNA samples are used for subsequent experimental genetic and genomic analysis.

(b) Tissue biopsy samples are recovered from a select group of patients at a major medical institution. As can be appreciated, biopsy samples may not be required for all disease conditions, and the method by which such samples are collected is dependent upon the specific biological condition under study. For example, in the study of hepatitis C (HCV), liver biopsy samples may be required to assist in the classification of the population into the various sub-populations as discussed above. Tissue samples may also be used for RNA extraction, to select appropriate candidate genes for genetic analysis, and to validate the biological effects of natural resistance mutations. Large-bore needle biopsies from liver transplantation patients and a select group of hemophiliacs and injecting drug users are recovered through a liver transplantation program. Additionally, infected and uninfected whole livers are obtained from either explanted organs during liver transplantation or from normal uninfected cadavers. Pre- and post-transplant biopsy samples may also be taken from implanted livers.

(5) Complete Additional Epidemiological Questionnaires

Additional population epidemiological information and individual supplemental medical and family histories are accessed through additional questionnaires. This information is used to develop an assessment of disease risk in individuals patients and throughout an entire population. As those skilled in the art can appreciate, the factors that are important to disease risk will vary from one disease or biological condition to another. Disease risk is essentially a statistical likelihood that a particular patient will contract a disease. The statistical likelihood is based on a number of implicated risk factors. Generally, there are well-established statistical approaches to defining and calculating the relative risk for a given patient based upon well-defined parameters that have been developed through previous epidemiological studies. Risk factors that are frequently included in the assessment are diet, smoking, anthropometry, alcohol/caffeine use, sexual activity, intravenous drug use, specific prescription drug use, family history, race, implicated genetic syndromes/diseases, occupational exposures, and medical history. Information relating to known risk factors is obtained, and these data are entered into the predefined data structure 204 (see FIG. 2).

Status and Risk Factor Analysis

For each disease or biological condition, a condition-specific protocol for the analysis of affected status and risk factors and is defined. As those skilled in the art can appreciate, different medical and biochemical analyses, that are reflective of different risk factors, are defined for each disease. For example, IV drug use may be an important risk factor in an HIV study, but may not be relevant in a serum cholesterol study.

Measurements indicative of affected status or an established risk factor are first identified and quantified. Many measurements or risk factors, such as viral load or serum concentration of a bio-molecule, are easily quantified. Measurements or risk factors (collectively, the metrics) that are not typically or easily quantified in a medical setting (for example, presence of jaundice in hepatitis patients) are assigned a numerical scale for ease of automated evaluation. The numerical scale may be nominal or ordinal depending upon whether the factor is dichotomous or is graduated. In an exemplary embodiment, nominal cases may be represented simply as 0 or 1 for false or positive result, respectively. In an exemplary embodiment of an ordinal case, a graduated measurement may be assigned to a scale from 0 to 10. In an exemplary embodiment of a normally continuous metric (such as serum cholesterol level), the metric may be represented in its conventional form (mg/dL for the cholesterol example). The invention is neither limited whether the metrics are continuous, nominal, or ordinal in nature nor by representation of a metric in a simpler form (for example, representing a continuous metric by an ordinal or nominal. Neither is the invention limited by the use of direct, indirect, or inferred measurements. For example, body mass index is a derivative of two anthropometric measurements. Established norms and ranges as well as accuracy and reliability estimates for each identified metric are based upon the medical literature. Expected and normal ranges for many metabolic, anthropometric, and clinical observations are widely available. Finally, all of the defined status or risk metrics and their numerical characteristics (definition, range, normal values, accuracy, etc.) are stored in the data structure 204 (see FIG. 2).

Criteria are identified through medical literature for each disease or condition status factor that account for the power of the factor to indicate the presence or absence of the biological condition of interest. Some tests, such as a positive result in HCV-EIA seroconversion test, are definitive in determining HCV affected status, while the affected status of other biological conditions, may be indicated, assumed, or implied by multiple factors or medical observations. That is, some tests may be more relevant to or predictive of the determination of affected status than other tests. The numeric values that indicate disease free status, mild disease, moderate disease, severe disease and the like are generally available from and based on previous clinical studies. For instance, very low serum cholesterol, indicative of a low risk for coronary artery disease, is usually defined in the medical literature as less than 130 mg/dL total lipid cholesterol. Moderate risk is defined by total lipid cholesterol of between 200 and 240 mg/dL. High coronary artery disease risk is defined by serum cholesterol concentrations of greater than 240 mg/dL.

Through examination of all relevant disease or condition indicators and their corresponding variation from unaffected to affected status, a numerical weighting function is developed that numerically combines all of the status metrics into a single score. The weighting function accounts for the relative importance of changes in each metric in terms of diagnosing the biological condition. One embodiment of the combined status scoring function might be a simple linear combination of the form $SS=A_ix'+A_2x_2+A_3x_3+\ldots A_ix_i$, where $A_1, A_2, A_3, \ldots A_i$ are weighting coefficients (and may each be positive or negative) for each of the numerical metric values $x_1, x_2, x_3, \ldots x_i$. SS is the overall status score. In general, the range and direction of positive affected status for the composite status score are irrelevant and will be implicitly defined by the weighting function. The invention is not limited by adopting the convention that increasing status score implies increasing severity of the biological condition. The invention is further not limited by the mathematical form of the weighting function; factors influencing the functional form may include, but are not limited by, the range and normal values of the metrics. A simplified example involving discrimination of hepatitis status might be $SS=10x_1+x_2$ where $x_1$ is a measurement of HCV antibody seroconversion, on a scale of 0 to 1, and x2 is a measure of viral titer, on a scale of 0 to 10. In this case, the scaling factor of 10 for $x_1$ represents a weighting adjustment to allow the seroconversion measurement to carry significant weight relative to viral titer. The weighting function and its parameters and components are stored in the data structure 204 (see FIG. 2).

It is important to note that since enrolled patients are reviewed over time and tests may be duplicated, the maximum result rather than a current time measurement result may be utilized for a given patient. This concept is important in keeping with the study design of attempting to identify ARU patients that possess protective mutations that prevent them from ever developing the condition in question. If a patient ever contracts a disease or condition, they must essentially be considered affected by the composite score described above.

Note that standard epidemiological practice allows for interpretation of the likelihood of contracting a condition in terms of either relative risk or odds ratios depending upon the specific situation under study. As one skilled in the art can appreciate, the principles underlying these discussions using one type of effect measurement are readily interpretable in terms of the remaining measurement. We will discuss the following in terms of risk ratios, but the present invention is not limited by this formulation and is intended to include formulation in terms of odds ratios.

Similarly to the status score calculation above, an analysis of the various risk factors relevant for the condition of interest is performed to provide a composite relative risk score. This portion of the definition will be guided by existing clinical and epidemiological studies that have identified the relative risk associated with each of the risk factors. Relative risk is typically defined as a ratio of the risk that a person with a certain risk factor will develop the condition, divided by the risk that a person without the risk factor will develop the condition. Relative risk measurements and incidence rates and computation thereof are well established and do not need to be reiterated here. Furthermore, the effects of confounding and interaction are managed using standard approaches as one skilled in the art can appreciate.

Certain risk factors are time sensitive and this aspect is usually accounted for in the epidemiological evaluation. An example of such a risk factor is the increased likelihood of lung cancer if one has ever smoked, although the risk declines over time as one remains smoke-free. For the purposes of the present invention, the composite relative risk score, RRS, is calculated in a manner analogous to the status score above, the only difference being that the metrics used for the risk score are quantified risk factors rather than affected status factors. The invention is not limited by the convention that increasing relative risk scores imply increasing likelihood of developing the condition of interest.

In the same fashion as the status score above, a variety of standard epidemiological and statistical formulae may be applied to calculate the composite relative risk score. The invention is not limited by the form of these calculations nor by the inclusion or exclusion of confounding or interacting factors. In an exemplary embodiment, previously defined relative risk analyses provide the optimal basis for the weighting coefficients when properly scaled by the normal and range values in the underlying risk factor measurement. In an extremely simplified example, consider a blood serum measurement that ranges from 75 to 300 mg/dL for which relative risk increases linearly from 1.0 to 3.0 at a measurement of 300. Also consider a second dichotomous risk factor (measured as 0 for negative, 1 for positive) that provides a relative risk of 2.0 for a positive result. In this case, it may be appropriate to assign a composite relative risk score formula of $RRS=3*x_1/300+2*x_2$, where $x_1$ is the blood serum measurement and $x_2$ is the binary risk factor measurement. In this illustrative example, the imbalance in measurement scale is addressed by dividing the serum measurement by 300 and the imbalance in relative risk is addressed by multiplying each risk factor score by its own independent relative risk factor. The relative risk weighting function and its parameters and components are stored in the data structure 204 (see FIG. 2).

It should be understood that the portion of the invention as just described is not an analysis of the condition of an individual patient, but a definition of the process to evaluate the affected status and relative risk of the selected biological condition. Once the foregoing procedures for evaluating relevant status factors, evaluating risk factors, and generating composite scores for each has been completed and stored in the data structure 204, test data (e.g., medical test results) for individuals may be subsequently entered into the data structure. The affected status and risk status composite scores may then be automatically determined for that individual and stored in the data structure 204.

Clinical Population Testing

Figure 4:
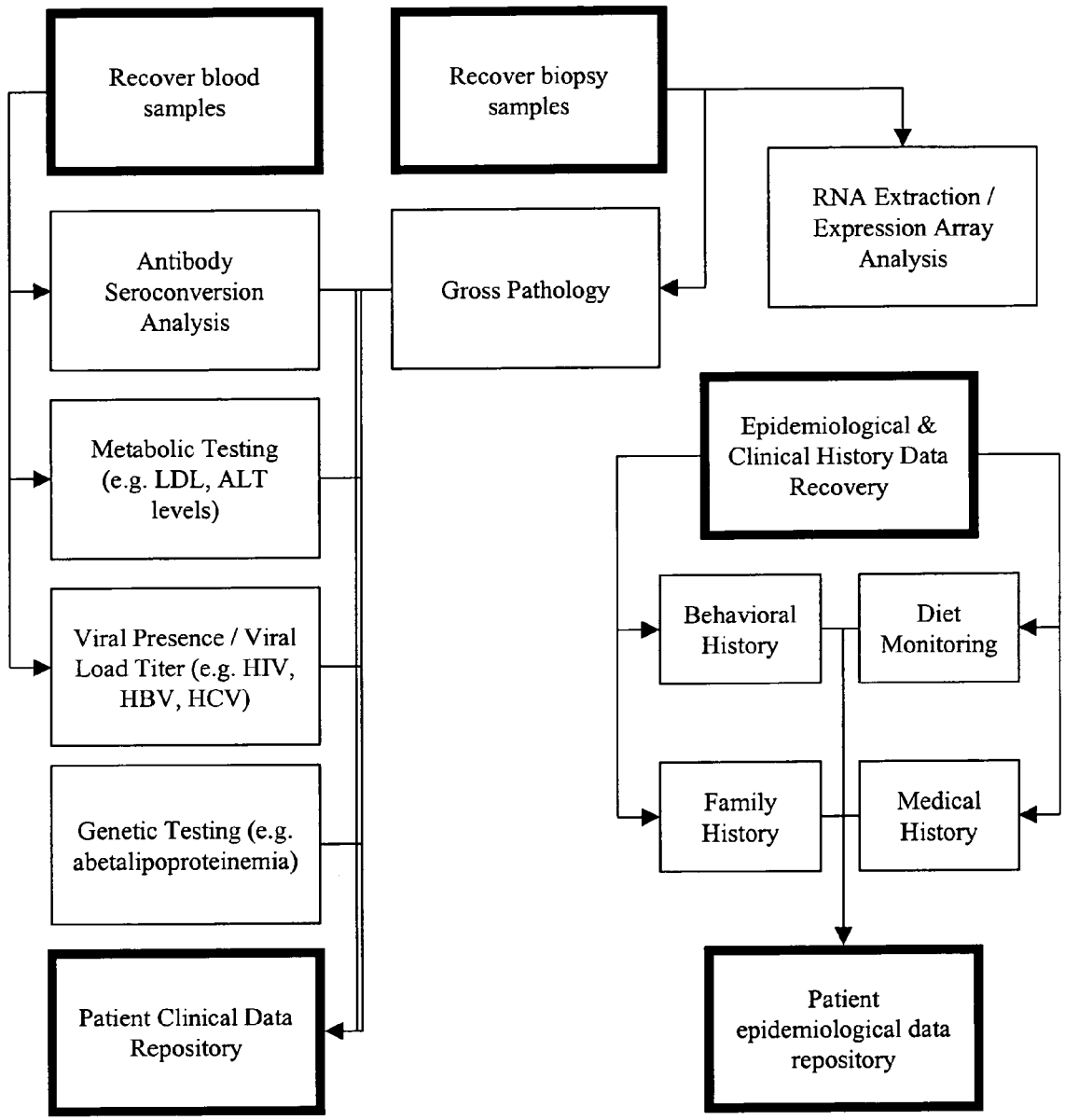
FIG. 4 is a flowchart illustrating the operation of the present invention to define a clinical population and characteristics indicative of a selected biological condition.

The following discussion provides details of steps that are taken to analyze a population and define affected status, risk factors and the characteristics of the ARA, ARU, and URU phenotypes. This process is also illustrated in the flow charts of FIG. 4. All information resulting from the following analyses is numerically evaluated as described above in the section entitled Status and Risk Factor Analysis and the results stored in the data structure 204 (see FIG. 2).

(1) Recovery of Blood Samples

Blood samples are recovered as described above. As noted above, different blood tests are relevant to different diseases. The relevance of various blood tests to different diseases may be determined on the basis of previous clinical studies and medical research. While some examples have been presented herein, those skilled in the art can appreciate that new tests may become available that are more highly relevant indicators of a particular affected status. Accordingly, the present invention is not limited by specific clinical blood tests or other medical tests that may presently be available or associated with particular diseases.

(2) Antibody Seroconversion Analysis

Figure 3:
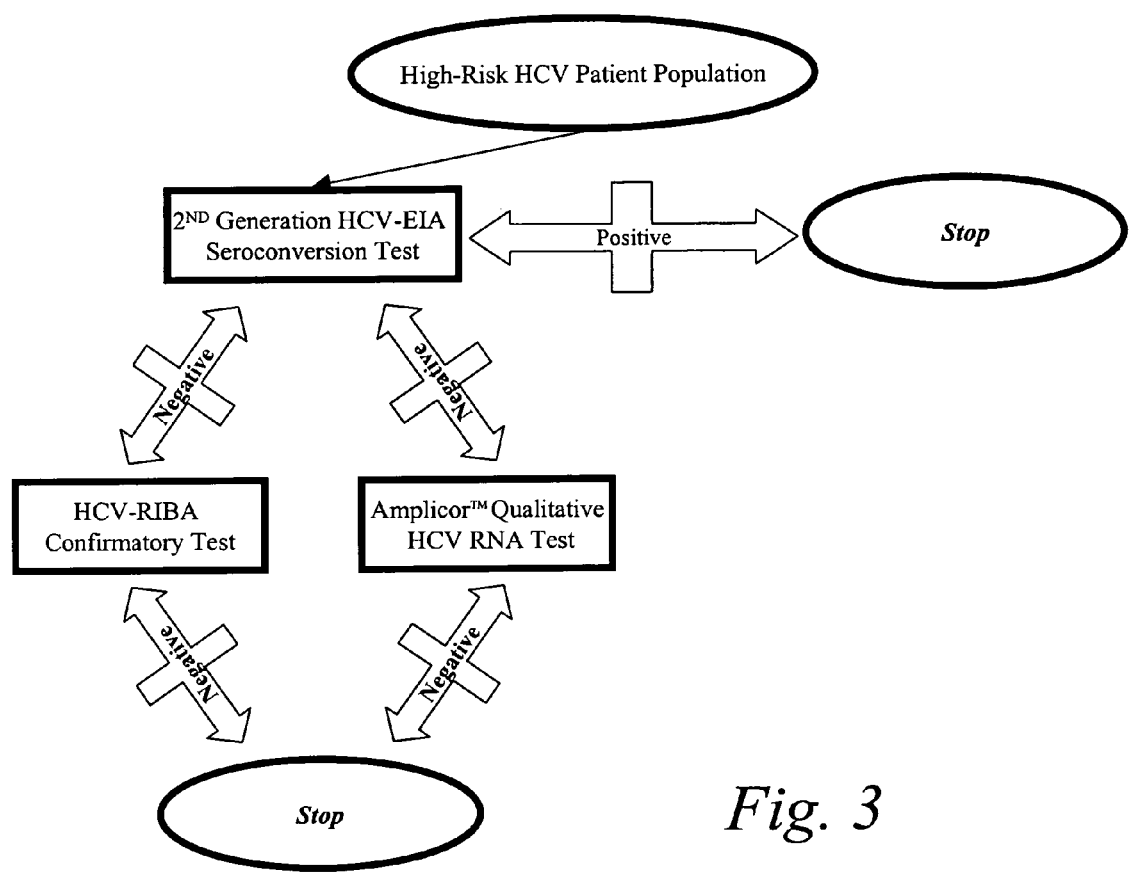
FIG. 3 is a flowchart illustrating one example of blood test analysis used to classify patients into predefined sub-populations.

In the case of infectious diseases, antibody seroconversion tests can be used to evaluate historical or current active viral infection. The invention employs standard and widely used clinical diagnostic tests. FIG. 3 illustrates an example of seroconversion analysis that may be used to classify a population when the biological condition of interest is hepatitis C. In the example of the HCV study, confirmatory second generation hepatitis C enzyme-link immuno-absorbant assay (EIA) tests are performed on all patients in the high-risk study populations. For those individuals testing positive for HCV-EIA, no further medical testing need be conducted. For those individuals testing negative for HCV-EIA, a confirmatory second test, the HCV radio-labeled recombinant immunoblot assay (RIBA) is performed as a negative HCV-EIA result is not definitive. Alternatively a qualitative HCV RNA test may be performed, as will be discussed in greater detail below. Patients testing negative for both immunoassays are retested and confirmed seronegative using the HCV-EIA approximately 15 weeks after their initial screening. Continued negative medical results or even a single positive result will be accounted for in the calculation of the composite status score for this individual.

(3) Metabolic Testing

Metabolic testing is used when appropriate to assist in stratifying clinical populations into the (ARA) and (ARU) sub-populations. Such metabolic tests are particularly important when the company seeks to identify drug targets associated with metabolic disorders such as diabetes and elevated or imbalanced serum cholesterol. In the example of the HCV study, the alanine aminotransferase (ALT) levels in clinical subjects are useful for the purpose of phenotype definition and disease monitoring. For other biological conditions of interest, different metabolic tests may be used. The various medical tests are selected for their relevance to defining the affected status of individuals in the population and will, of course, vary from one selected biological condition to another.

The present invention is not limited by a specific selected biological condition or specific medical tests used to determine the affected status of members of the population.

(4) Viral Presence/Viral Load Analysis

Analysis of infectious diseases may also involve the use of PCR-based tests to qualitatively and quantitatively analyze viral presence and viral load, respectively. These tests are used to further confirm the (ARU) phenotype, and they are of particular utility in study subjects who are immuno-compromised because of the presence of HIV infection, drug use, stem cell disease, or other disease. For example, the Roche Amplicor™ HCV RNA screening test can be used to confirm seronegative status in the phenotypically stratified (ARU) sub-population of subjects in the HCV study. This is illustrated in the chart of FIG. 3.

(5) Genetic Testing

In some cases, it is necessary to rule out known genetic causes of the ARU phenotype in a population of subjects. For instance, a variety of genetic diseases have as an associated phenotype of hypolipidemia (e.g., abetalipoproteinemia, Tangier's Disease, etc.). In the specific case whereby an evaluation of serum cholesterol levels is at issue, these abetalipoproteinemia and other genetic diseases must be excluded as an alternate cause of the ARU phenotype. For selected biological conditions having potential genetic causes, genetic tests are used to rule out these known genetic illnesses as contributing factors within the ARU population pool. Wherever possible, this analysis is carried out using standard and well established genetic tests. However, the present invention is intended to encompass new genetic analysis techniques that may be discovered and that help to differentiate a population into the phenotypic groups described above. While the genetic tests themselves are not the subject of the present invention, these tests are used to define and classify sub-populations in accordance with the principles of the present invention. Accordingly, the present invention is not limited by the specific genetic tests that are presently available or may become available in the future.

(6) Patient Clinical Data Repository

Data from all serological testing is appended to the data structure 204 (see FIG. 2). This data may include metabolic blood measurements, such as enzyme measurements, cholesterol, white blood cell count, vitamin sufficiency, antibody/viral measurements, and the like.

(7) Gross Pathology

Biopsy samples from target organs are recovered according to the techniques described above. As noted above, biopsy samples may not be required for all disease conditions. In some cases, biopsy samples from target affected organs are recovered and analyzed for the presence and degree of severity of the disease under study. These data are used in defining both the ARA and ARU population subgroups, and in associated experiments designed to develop candidate gene lists and thereby enable the drug development programs. In the specific case of the hepatitis C study, liver biopsy samples are evaluated for evidence of HCV infection, liver disease, hepatocyte necrosis, inflammation, and bridging and portal fibrosis. Cirrhosis of the liver may provide important pathological information in other disease studies. These data are used to evaluate the grade and stage of liver disease in study participants. As noted above, the purpose of this analysis is to define the characteristics of various phenotypes for a particular disease. At this stage of analysis, individuals in the population are not necessarily categorized into a sub-population. Rather, the characteristics of the various sub-populations are defined by analyzing relevant medical tests and risk factors for a particular disease.

(8) RNA Extraction and Expression Array Analysis

RNA is extracted from tissue samples to support expression array analysis for the development of candidate gene lists, to validate protective mutations, and for drug development efforts.

(9) Epidemiological and Clinical History Data Recovery

In addition to the existing epidemiological, clinical, and other data previously collected from study subjects by clinical researchers as described above, additional epidemiological questionnaires are developed that are tailored to the specific disease of interest. These data are used to assist in stratifying populations into the various phenotypic subgroups. These population questionnaires may include but are not limited to interrogatories of the following types:

(a) Behavioral History

A comprehensive patient history is collected regarding certain predisposing or ameliorating behaviors among individuals in the study population. In the HVC example, behaviors involving injecting drug use, needle sharing behaviors, drug injecting partners, sexual histories, and potential occupational exposures are investigated.

(b) Diet Monitoring

When the invention is applied to the study of metabolic disorders or other conditions that are known to have a contributing dietary risk component, additional clinical histories are collected to specifically address these risk factors. The use of standardize diet questionnaires may be utilized to assess the patient's dietary intake. In some cases, the patient may be asked to participate in short term dietary monitoring to address the importance of dietary risk factors over a period of normal food consumption lasting several weeks or more.

(c) Family History

Additional family medical histories are frequently collected to assess the importance of genetics to individual expression of both the ARA and ARU phenotypes. The statistical genetics component of this invention is especially benefited from the combined data of sib-pairs and families. Therefore, a special emphasis is placed on accessing and evaluating clinical histories from siblings and other close family members. For instance, in the case of hepatitis C infection, sib pairs that are both affected with hemophilia and have similar medical histories with respect to this disease are expected to be of particular importance in contributing statistical power to this analysis.

(d) Medical History

Additional medical histories are obtained where applicable in order to facilitate the placement of individuals into the ARA and ARU phenotypic subgroups. With respect to hepatitis C infection in hemophiliac populations, time, duration of use, and date of administration of clotting factors is of particular importance. For other hepatitis C study participants, the presence of other infectious and/or sexually transmitted diseases is of importance, as well as is a history of hemodialysis, blood transfusion, or other possible nosocomial, occupational, or household exposures.

All additional medical, family, dietary, and behavioral histories are appended to data structure 204 (see FIG. 2) designed for the purpose of monitoring these potential exposures.

Individual Subject Analysis and Classification

Figure 5:
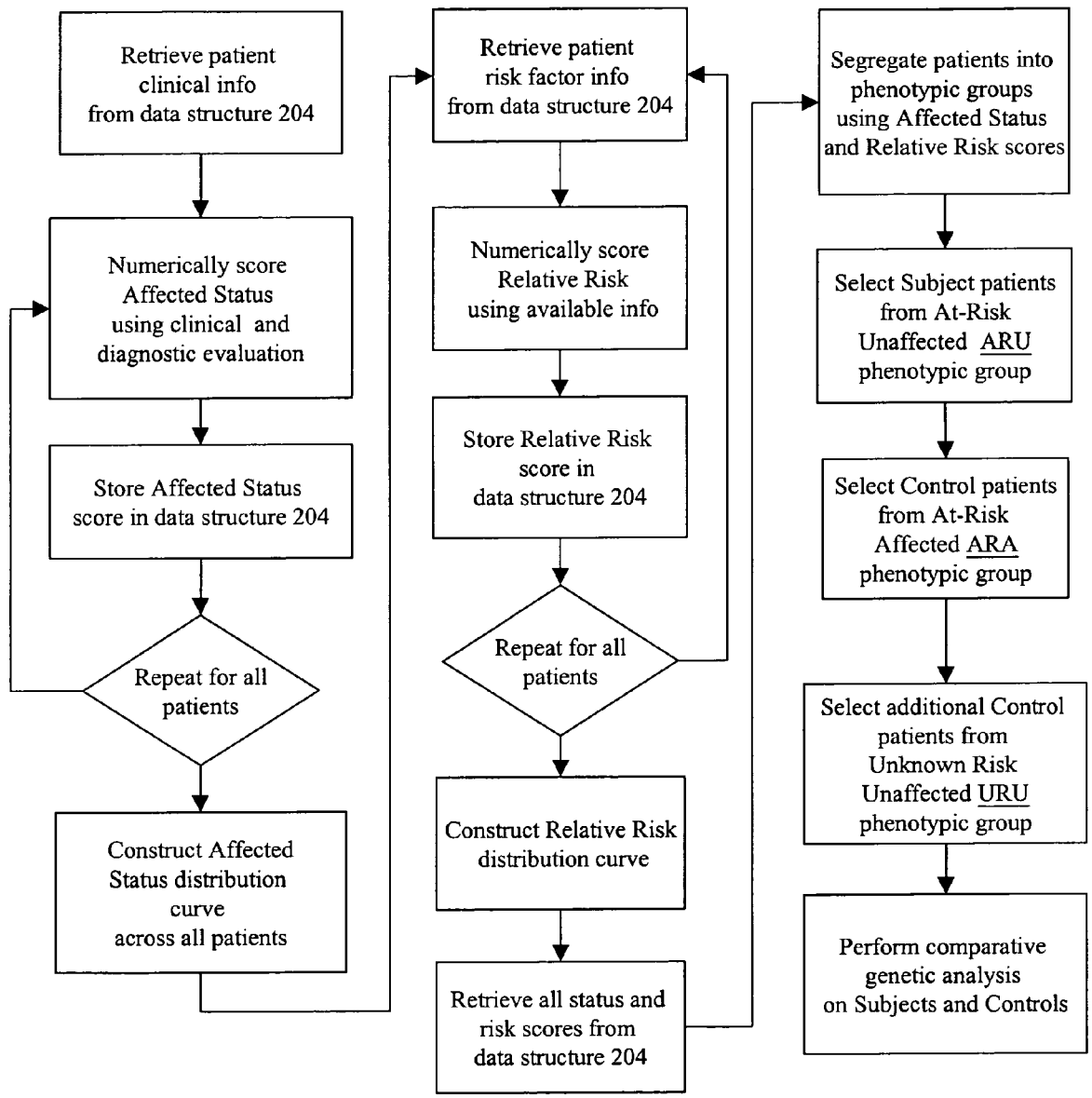
FIG. 5 is a flowchart illustrating the operation of the present invention to categorize individuals into sub-populations based on predefined characteristics.

Once the status factors and risk factors characteristic of a particular biological condition's phenotype have been determined and the relevant medical tests and epidemiological questions defined, the results of this analysis may be applied to individuals within a population so as to classify the individuals into various phenotypic groups. As noted above, medical tests scores and other factors may be numerically rated and weighted based on the sensitivity and specificity of each test for defining the desired phenotypic condition. Similarly, epidemiological data is numerically rated to define risk status for the biological condition of interest. Thus, the previous discussion is directed to the definition of procedures for evaluating each individual for the status and risk associated with a particular disease or condition The following discussion is directed to the analysis of specific medical test results, medical histories, and epidemiology for an individual, and the assignment of numerical scores for status and risk factors. As discussed previously and detailed below, the individual will be classified into one of the sub-populations based upon composite numerical scores. This process is also illustrated in the flowcharts of FIG. 5.

The individual patient's affected status factors (such as medical test results and clinical evaluation results) are assigned a numeric score based on the previous definition of status factors for the present condition. Similarly, the individual patient's risk factors (including medical history and epidemiological questionnaire responses) are numerically scored to determine relative risk status for the biological condition of interest.

(1) Clinical information (test results, physician evaluation, medical history results) relating to a study patient is retrieved from the data structure 204 (see FIG. 2).

(2) The patient's affected status is numerically scored using the composite status score approach described in the foregoing. The composite status score will indicate the degree of disease progression, from no evidence of disease to severe disease.

(3) Affected status score is stored in the data structure 204 (see FIG. 2).

(4) Repeat steps (1)-(3) for each patient. Following the completion of steps (1)-(3) for each patient in the population, the data structure 204 will contain numeric scores indicating affected status for the entire clinical population.

Figure 6:
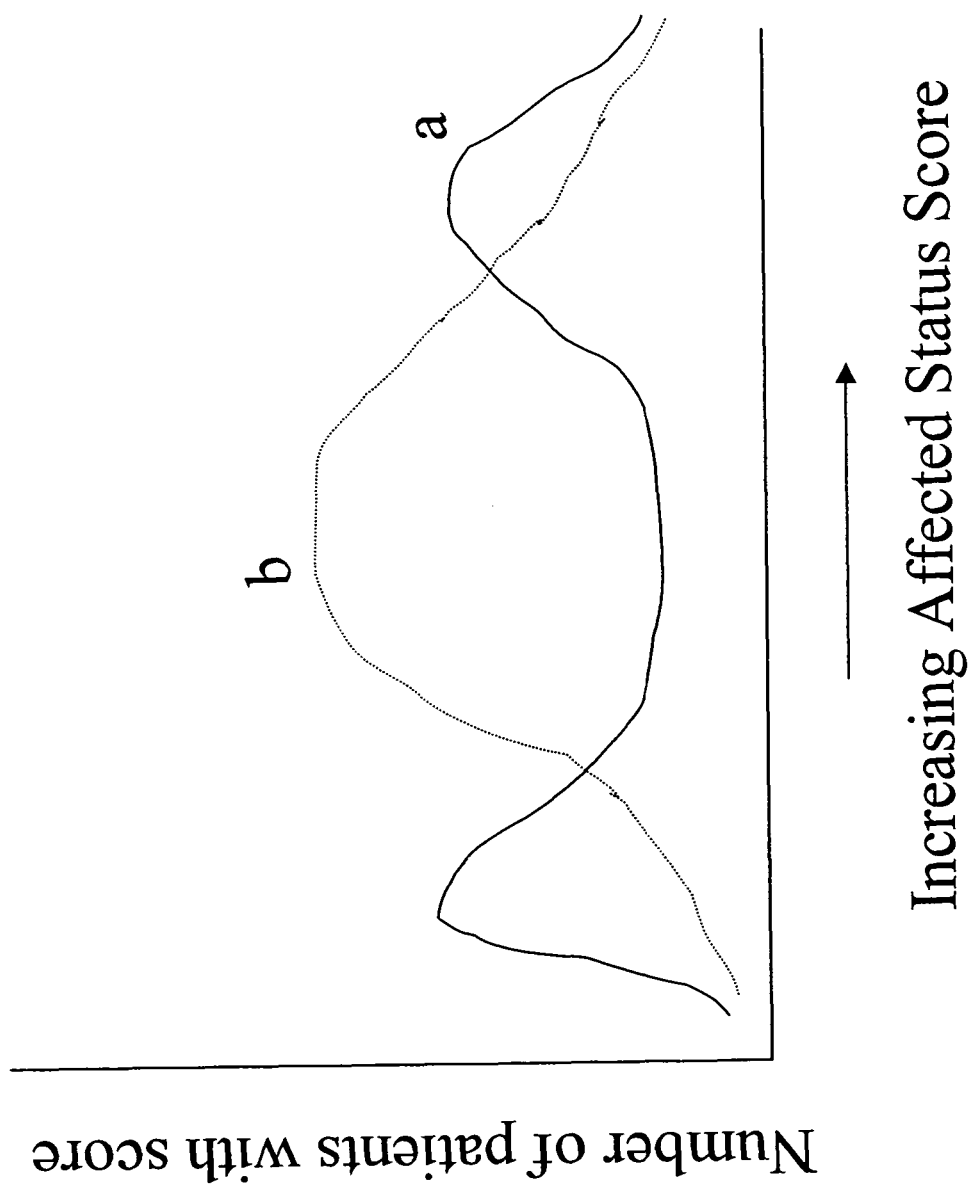
FIG. 6 is a sample frequency distribution plot illustrating affected status for a selected biological condition.

(5) An affected status distribution curve may be constructed across all available patients. FIG. 6 shows two hypothetical examples of affected status distributions; one (a) from a hypothetical infectious disease illustrating an essentially dichotomous infected-uninfected distribution, and the other (b) from a hypothetical metabolic disease where the status is determined from continuous measurements that center around a "normal" value. These distributions are illustrative only and the invention is not limited by the form of the distribution in any case.

(6) Medical history and epidemiological information regarding a patient is retrieved from the data structure 204 (see FIG. 2).

(7) Using this information, numerically score relative risk for the patient using the relative risk score approach described in the foregoing. The composite score will provide a quantifiable indication of whether this individual is more or less likely than someone in the general population to succumb to the condition of interest.

(8) Store composite relative risk score in the data structure 204 (see FIG. 2).

Figure 7:
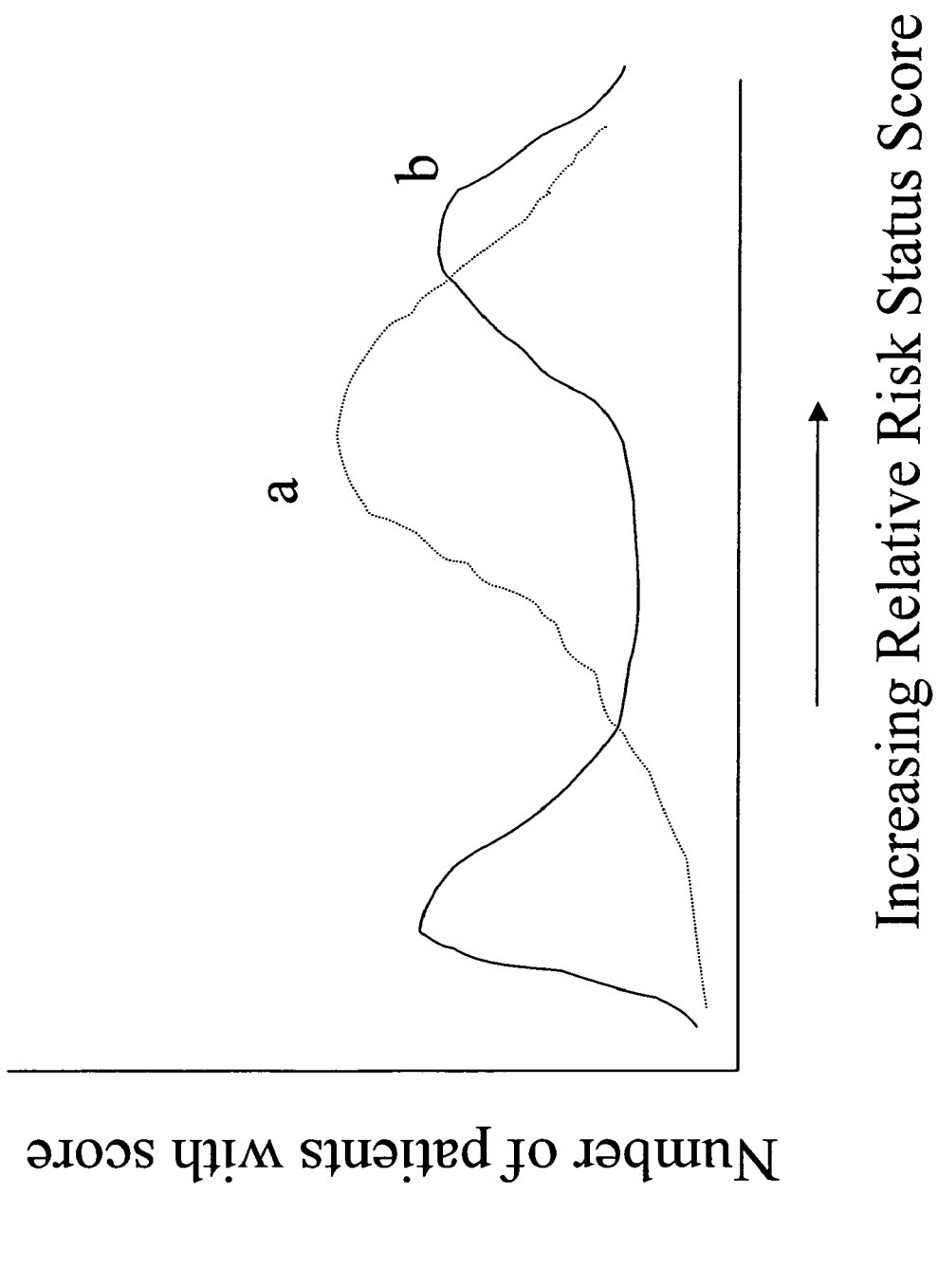
FIG. 7 is a frequency distribution plot illustrating risk status for a selected biological condition.

(9) Repeat steps (6)-(8) for each patient. Following the completion of steps (6)-(8), each patient in the population will have a numeric score that indicates composite relative risk from all known risk factors. A distribution curve may be constructed for the composite relative risk across the population. FIG. 7 shows two examples of hypothetical composite relative risk curves; one (a) where relative risk is generally skewed toward high risk, possibly due to high-risk population bias, and another (b) where the risk is due to essentially dichotomous risk factors such as exposure to an infectious individual. These distributions are illustrative only and the invention is not limited by the form of the distribution in any case.

As will be discussed below, the numeric scores for affected status and risk status for each patient are analyzed so that each patient may be categorized into one of the selected phenotypic sub-populations.

(10) Retrieve stored scores for affected status and risk for each patient from the data structure 204.

Figure 8:
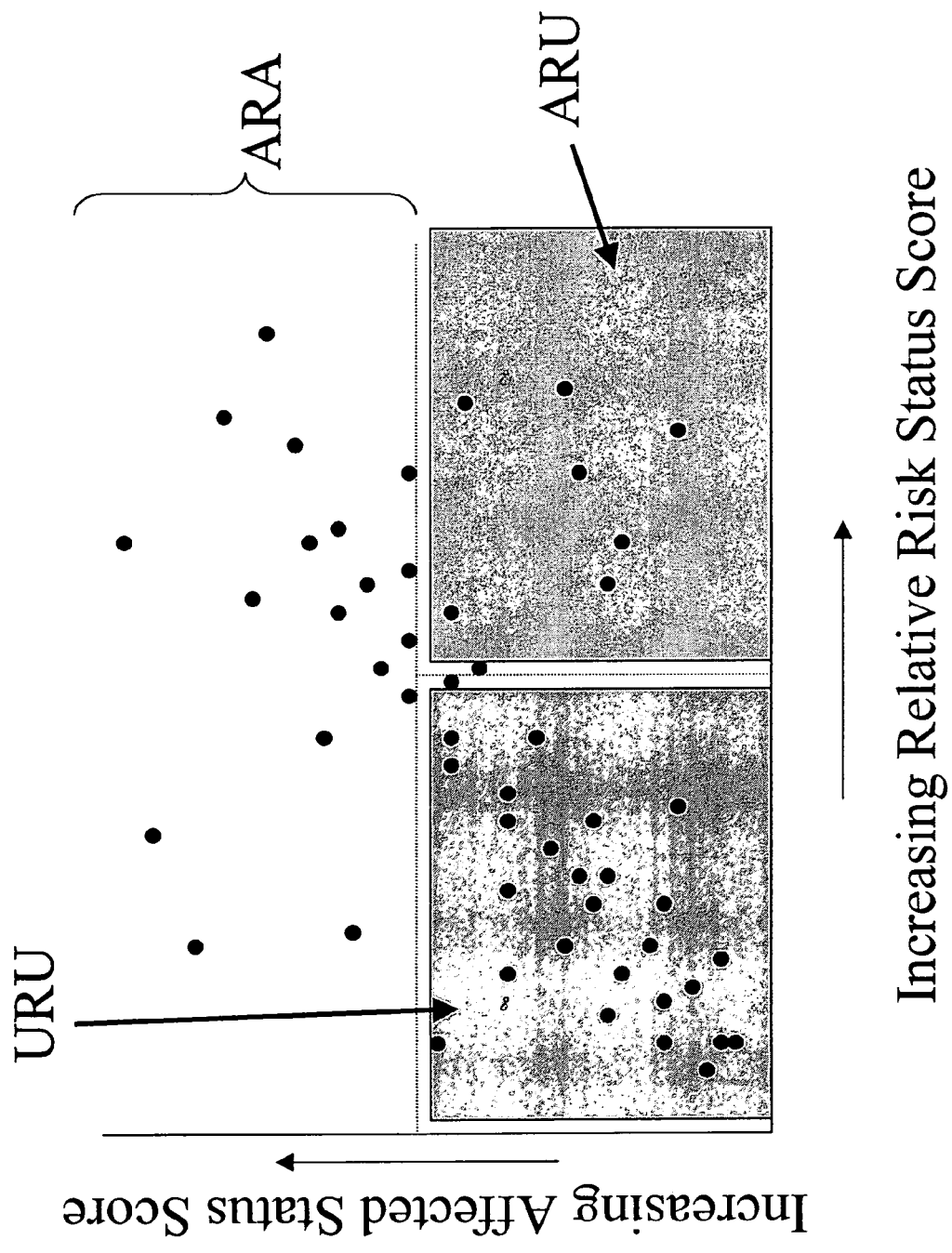
FIG. 8 is a plot of affected status scores and risk scores that illustrate the classification of individuals into sub-populations.

(11) The patients are segregated into the three phenotypic classifications At-Risk Unaffected (ARU), At-Risk Affected (ARA), and Unknown Risk Unaffected (URU) by analysis of each individual's composite affected status and relative risk scores in comparison with those of the entire population. In one embodiment, the two scores may be plotted parametrically for each patient, as shown in FIG. 8. Therein, an example is shown of an underlying correlation between increasing risk and increasing affected status (or severity). Superimposed upon this primary correlation are outlier patients representing various combinations of risk and affected status. FIG. 8 also hypothetically illustrates regions designated as ARU, ARA, and URU providing one graphical method for delineating patient inclusion into each phenotypic class. In another embodiment, the affected status and relative risk scores for each individual may be further consolidated into a single score and distributions thereof utilized to classify the patients into phenotypic groups. The invention is not limited by the precise mathematical method utilized to delineate the regions of ARU, ARA, and URU patients, and one skilled in the art will recognize a number of approaches suitable for this purpose. These may include, but are not limited to, correlation or regression type analyses.

(12) Select a desired number of control patients, for further study, from the subset of patients classified as being At Risk Affected (ARA). In one embodiment, these patients are randomly chosen from a prescribed percentage in the tail of the affected status distribution representing severely affected individuals. The invention is not limited by the method used for selecting these control patients from the ARA group. The number of control patients thus selected and the prescribed percentage of the affected status distribution from below which they are selected will vary by condition and population. Achievement of statistical significance in the final analysis of variant and functional bin frequencies will be a major controlling factor in establishing these values. Other controlling factors will include but not be limited to total population size, sensitivity and specificity of status measurements, and bias of the population toward affected or unaffected status.

(13) Select an additional number of control patients from the Unknown Risk Unaffected group identified in (11) above. In one exemplary embodiment, the selection may be made randomly. As with the ARA controls in (12), the number of additional controls selected may vary by condition and population. This number will also be significantly affected by the requirements of statistical significance in the variant or functional bin analysis. The invention is neither limited by the method used to select these additional controls from the URU group nor by the number selected.

(14) Select a number of study patients from the at-risk unaffected (ARU) group. In one exemplary embodiment the study patients may be selected randomly from the entire ARU sub-group. In another embodiment, an intermediate measure may be utilized to sort the ARU patients. This intermediate measure may be based upon degree of risk, severity of affected status, or a combination of the two. The invention is neither limited by the method used to select the study patients from the ARU group nor by the number selected. As has been discussed above, the paradigm put forth by the present invention is that patients in the ARU sub-population are believed to benefit from a genetic mutation that confers a medical benefit that allows them to remain disease-free for a selected biological condition, despite the fact that the individuals patients in this sub-population are at high risk for the disease. The invention thereby forms the basis for a strategy by which such protective mutations, when identified, can be replicated by pharmaceutical agents.

(15) Proceed to genetically analyze the study subjects (the selected ARU patients) relative to the controls (the combination of selected ARA and URU patients) for evidence of specific association of variants or functional bins with the ARU study subject group. The classification of patients into sub-populations, particularly the ARU sub-population, permits a new paradigm for drug target discovery. That is, the classification of patients into the ARU sub-population allows genetic analysis to focus on the reasons that a particular sub-population remains healthy in spite of being at significant risk for the biological condition of interest. This is a significant departure from the conventional paradigm where the disease state itself is genetically analyzed. Thus, the ideal drug is one that mimics the operation of protective mutations that confer resistance to disease in the ARU sub-population. Similarly, as one skilled in the art can appreciate, the knowledge gained from this genetic analysis can also form the basis for diagnostic assay or vaccine development.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A computer-implemented method for the identification of a drug target associated with a selected biological condition, comprising: using a computer to analyze stored data related to medical histories of a population;
    using a computer to analyze stored data related to medical test results for the population; and
    based on computer analysis of the data related to the medical histories and the data related to the medical test results, classifying the population into at least two phenotypic sub-populations defined as
        at risk and affected (ARA), whose members have ever been affected by the selected biological condition, and
        at risk and unaffected (ARU), whose members ought to be affected by the selected biological condition at the present time based on a risk analysis, but are unaffected by the selected biological condition at the present time;
    performing a computer analysis of genetic data from the ARA sub-population and the ARU sub-population to identify genetic variations therebetween;
    displaying the data for a user; and
    using data related to the identified genetic variations between the ARA sub-population and the ARU sub-population to identify the drug target associated with the selected biological condition.

2. The method of claim 1, further comprising generating statistical data related to the medical histories and the medical test results wherein classifying the population comprises analyzing the statistical data.

3. The method of claim 1 wherein analyzing medical histories comprises assigning numerical scores to selected conditions associated with the selected biological condition.

4. The method of claim 1 wherein analyzing medical test results comprises assigning numerical scores to selected medical tests associated with the selected biological condition.

5. The method of claim 1 wherein analyzing medical histories and medical test results comprises assigning numerical scores to selected conditions associated with the selected biological condition and analyzing medical test results comprises assigning numerical scores to selected medical tests associated with the selected biological condition.

6. The method of claim 5 wherein classifying the population comprises evaluating the numerical scores for the medical histories and the medical test results.

7. The method of claim 6 wherein classifying the population comprises combining the numerical scores for the medical histories and the medical test results and classifying the population based on the combined numerical scores.

8. The method of claim 5, further comprising generating statistical data related to the numerical scores for the medical histories and the medical test results wherein classifying the population comprises analyzing the statistical data.

9. The method of claim 8 wherein the statistical data comprises generating a frequency distribution plot related to the numerical scores for the medical histories and the medical test results.

10. The method of claim 1, further comprising comparing the medical histories and the medical test results of the sub-population classified as ARU with the medical histories and the medical test results of the sub-population classified as ARA.

11. The method of claim 1, further comprising selecting the portion of the sub-population classified as ARA and using the selected portion as a control group.

12. The method of claim 1 wherein classifying the population further comprises classifying the population into the ARA sub-population, the ARU sub-population or a phenotypic sub-population defined as unknown risk and unaffected (URU) by the selected biological condition.

13. The method of claim 12, further comprising comparing the medical histories and the medical test results of the sub-population classified as ARU with the medical histories and the medical test results of the sub-population classified as URU.

14. The method of claim 12 wherein the medical test results comprises genetic test results, the method further comprising comparing the genetic test results of the sub-population classified as ARU with the genetic test results of the sub-population classified as URU.

15. The method of claim 14, further comprising determining genetic differences between genetic test results of the sub-population classified as ARU with the genetic test results of the sub-population classified as URU.

16. The method of claim 15, further comprising identifying drug targets based on the genetic differences between genetic test results of the sub-population classified as ARU with the genetic test results of the sub-population classified as URU.

17. The method of claim 1 wherein identifying a target comprises identifying a drug target based on the genetic variations between genetic test results of the group of subjects classified as ARU with the genetic test results of the group of subjects classified as ARA.

18. The method of claim 1 wherein identifying a target comprises identifying a diagnostic assay based on the genetic variations between genetic test results of the group of subjects classified as ARU with the genetic test results of the group of subjects classified as ARA.

19. The method of claim 1 wherein identifying a target comprises identifying a vaccine based on the genetic variations between genetic test results of the group of subjects classified as ARU with the genetic test results of the group of subjects classified as ARA.

20. The method of claim 1 wherein identifying a target comprises identifying a candidate drug based on the genetic variations between genetic test results of the group of subjects classified as ARU with the genetic test results of the group of subjects classified as ARA.

21. A computer-implemented method of data analysis to identify a target for use in treating a disease, comprising:
  defining disease characteristics of the disease, including medical tests associated with the disease;
  performing a computer analysis of medical test results based on medical tests performed on biological samples from a plurality of subjects with respect to the defined characteristics of the disease;
  based on the analysis, determining an affected status of each of the plurality of subjects;
  defining risk characteristics of the disease;
  based on the risk characteristics, determining a risk status of each of the plurality of subjects;
  based on the affected status and the risk status, classifying each of the plurality of subjects into a predetermined category for the disease selected from a group comprising at risk, affected (ARA), whose members have ever been affected by the disease, and at risk, unaffected (ARU), whose members remain unaffected by the disease and whose unaffected status is inconsistent with the risk status;
  performing genetic tests on the plurality of subjects in a panel of candidate genes suspected to be relevant to the disease;
  identifying functional variants in at least one of the candidate genes in the plurality of subjects;
  analyzing the genetic test results of the group of subjects classified as ARU with the genetic test results of the group of subjects classified as ARA to identify one or more statistically significant functional variants where the allele frequency is statistically larger in the group of subjects classified as ARU as compared to the allele frequency in the group of subjects classified as ARA;
  thereby identifying each candidate gene containing one of the said statistically significant functional variants as a drug targets for use in treating the disease;
  and displaying each of the identified target candidate genes to a user.

22. The method of claim 21 wherein the defined disease characteristics of the disease have associated numerical scores and determining the affected status of each of the plurality of subjects comprises determining numerical scores based on the analysis of the medical test results.

23. The method of claim 21 wherein the defined risk characteristics of the disease have associated numerical scores and determining the risk status of each of the plurality of subjects comprises determining numerical scores.

24. The method of claim 21 wherein the defined disease characteristics of the disease have associated numerical scores and the defined risk characteristics of the selected biological condition have associated numerical scores, the classification of each of the plurality of subjects into a predetermined category being based on the numerical scores for affected status and risk status.

25. The method of claim 24 wherein the numerical scores for affected status and risk status are combined to form a combined numerical score, the classification of each of the plurality of subjects into a predetermined category being based on the combined numerical scores for affected status and risk status.

26. The method of claim 21 wherein the medical tests associated with the disease have varying degrees of relevance in defining the disease characteristics, the method further comprising assigning relevance weighting factors to the medical tests based on the degree of relevance, the affected status being based on the weighted medical tests.

27. The method of claim 21, further comprising generating statistical data related to the affected status and risk status wherein classifying each of the plurality of subjects into a predetermined category comprises analyzing the statistical data.

28. The method of claim 21 wherein risk status is determined at least in part from medical histories of the plurality of subjects, the method further comprising comparing the medical histories and the medical test results of the group of subjects classified as ARU with the medical histories and the medical test results of the group of subjects classified as ARA.

29. The method of claim 21 wherein identifying one or more targets comprises identifying a drug target based on the genetic differences between genetic test results of the group of subjects classified as ARU with the genetic test results of the group of subjects classified as ARA.

30. The method of claim 21 wherein identifying one or more targets comprises identifying a diagnostic assay based on the genetic differences between genetic test results of the group of subjects classified as ARU with the genetic test results of the group of subjects classified as ARA.

31. The method of claim 21 wherein identifying one or more targets comprises identifying a vaccine based on the genetic differences between genetic test results of the group of subjects classified as ARU with the genetic test results of the group of subjects classified as ARA.

32. The method of claim 21 wherein the plurality of subjects are classified into a category selected from a group comprising at-risk, affected (ARA), unknown risk, unaffected (URU), and at risk unaffected (ARU).

33. The method of claim 32 wherein risk status is determined at least in part from medical histories of the plurality of subjects, the method further comprising comparing the medical histories and the medical test results of the group of subjects classified as ARU with the medical histories and the medical test results of the group of subjects classified as URU.

34. The method of claim 32 wherein the medical test results comprises genetic test results, the method further comprising comparing the genetic test results of the group of subjects classified as ARU with the genetic test results of the group of subjects classified as UFU.

35. The method of claim 34, further comprising determining genetic differences between genetic test results of the group of subjects classified as ARU with the genetic test results of the group of subjects classified as URU.

36. The method of claim 35, further comprising identifying a drug target based on the genetic differences between genetic test results of the group of subjects classified as AFU with the genetic test results of the group of subjects classified as URU.

37. The method of claim 36, further comprising identifying a diagnostic assay based on the genetic differences between genetic test results of the group of subjects classified as ARU with the genetic test results of the group of subjects classified as URU.

38. The method of claim 36, further comprising identifying a vaccine based on the genetic differences between genetic test results of the group of subjects classified as ARU with the genetic test results of the group of subjects classified as URU.

39. The method of claim 20 wherein identifying a target comprises identifying a candidate drug based on the genetic variations between genetic test results of the group of subjects classified as ARU with the genetic test results of the group of subjects classified as ARA.

40. A system for data analysis to identify a target for treating a selected biological condition, comprising:

a affected status data structure containing numerical data defining disease characteristics of the selected biological condition, including medical tests associated with the selected biological condition;

a disease risk data structure containing numerical data defining disease risk characteristics of the selected biological condition; and a processor to:

accept medical test results from a plurality of subjects and assign affected status numeric scores to the medical test results based on the numerical data defining disease characteristics of the selected biological condition;

store the affected status numeric scores for each of the subjects in the affected status data structure;

accept medical history data from a plurality of subjects and assign current disease risk numeric scores to the medical history data based on the numerical data defining disease risk characteristics of the selected biological condition;

store the disease risk numeric scores for each of the subjects in the disease risk data structure;

determine an affected status and risk status for each of the subjects based on the respective affected status numeric scores and the current disease risk numeric scores;

based on the affected status and the risk status, classify each of the plurality of subjects into a predetermined category selected from a group of categories comprising at risk, affected (ARA) and at risk unaffected (ARU);

analyze genetic test result data to determine genetic differences between the subjects in the ARA category and subjects in the ARU category; and identify a target for treating the selected biological condition.

41. The system of claim 40 wherein the processor combines the numerical scores for affected status and risk status to form a combined numerical score, the processor further classifying of each of the plurality of subjects into a predetermined category being based on the combined numerical scores for affected status and risk status.

42. The system of claim 40 wherein the medical tests associated with the selected biological condition have varying degrees of relevance in defining the disease characteristics, the processor further assigning relevance weighting factors to the medical tests based on the degree of relevance, the processor determining the affected status based on the weighted medical tests.

43. The system of claim 41 wherein the processor further generates statistical data related to the affected status and risk status, the processor further classifying of each of the plurality of subjects into a predetermined category being based on the combined numerical scores for affected status and risk status based on analysis of the statistical data.

44. The system of claim 41 wherein the processor further classifies each of the plurality of subjects into a predetermined category selected from a group of categories comprising at-risk, affected (ARA), unknown risk, unaffected (URU), and at risk unaffected (ARU).

45. The system of claim 40 wherein the processor is configured to identify a drug target based on the genetic variations between genetic test results of the group of subjects classified as ARU with the genetic test results of the group of subjects classified as ARA.

46. The system of claim 40 wherein the processor is configured to identify a candidate drug based on the genetic variations between genetic test results of the group of subjects classified as ARU with the genetic test results of the group of subjects classified as ARA.

47. The system of claim 40 wherein the processor is configured to identify a diagnostic assay based on the genetic variations between genetic test results of the group of subjects classified as ARU with the genetic test results of the group of subjects classified as ARA.

48. The system of claim 40 wherein the processor is configured to identify a vaccine based on the genetic variations between genetic test results of the group of subjects classified as ARU with the genetic test results of the group of subjects classified as ARA.

* * * * *